United States Patent
Wald et al.

(10) Patent No.: US 12,290,323 B2
(45) Date of Patent: May 6, 2025

(54) POINT-OF-CARE MAGNETIC RESONANCE IMAGING SYSTEM FOR LUMBAR PUNCTURE GUIDANCE

(71) Applicant: The General Hospital Corporation, Boston, MA (US)

(72) Inventors: Lawrence L. Wald, Cambridge, MA (US); Clarissa Zimmerman-Cooley, Boston, MA (US); Patrick C. McDaniel, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 165 days.

(21) Appl. No.: 17/996,852

(22) PCT Filed: Apr. 26, 2021

(86) PCT No.: PCT/US2021/029193
§ 371 (c)(1),
(2) Date: Oct. 21, 2022

(87) PCT Pub. No.: WO2021/217144
PCT Pub. Date: Oct. 28, 2021

(65) Prior Publication Data
US 2023/0136830 A1    May 4, 2023

Related U.S. Application Data

(60) Provisional application No. 63/015,266, filed on Apr. 24, 2020.

(51) Int. Cl.
*A61B 34/20* (2016.01)
*A61B 5/00* (2006.01)
(Continued)

(52) U.S. Cl.
CPC ............. *A61B 34/20* (2016.02); *A61B 5/004* (2013.01); *A61B 5/055* (2013.01);
(Continued)

(58) Field of Classification Search
CPC ......... A61B 34/20; A61B 5/004; A61B 5/055; A61B 2017/3405; A61B 2560/0431;
(Continued)

(56) References Cited

U.S. PATENT DOCUMENTS

| | | |
|---|---|---|
| 6,411,187 B1 | 6/2002 | Rotem et al. |
| 10,359,481 B2 | 7/2019 | Wald et al. |

(Continued)

OTHER PUBLICATIONS

International Search Report in PCT/US2021-029193; received on Aug. 18, 2021.

*Primary Examiner* — Alexei Bykhovski
(74) *Attorney, Agent, or Firm* — QUARLES & BRADY LLP

(57) ABSTRACT

A single-sided magnet and magnetic resonance imaging ("MRI") system are portable and lightweight, enabling use as a point-of care ("POC") MRI device. The portable MRI system includes a magnet assembly containing layers of magnet blocks, such as rare-earth magnet blocks. The magnet blocks are arranged in concentric rings in each layer, and surround a central aperture extending through the magnet assembly. The central aperture is sized to allow a medical instrument, such as a needle, to pass through the central aperture. The portable MRI system can therefore be used for image guidance in lumbar puncture ("LP") and other medical procedures.

21 Claims, 6 Drawing Sheets

(51) Int. Cl.
*A61B 5/055* (2006.01)
*G01R 33/38* (2006.01)
*G01R 33/383* (2006.01)
*G01R 33/385* (2006.01)
*A61B 17/34* (2006.01)

(52) U.S. Cl.
CPC ....... *G01R 33/3808* (2013.01); *G01R 33/383* (2013.01); *G01R 33/385* (2013.01); *A61B 2017/3405* (2013.01); *A61B 2560/0431* (2013.01)

(58) Field of Classification Search
CPC .............. A61B 5/4566; A61B 2505/05; G01R 33/3808; G01R 33/383; G01R 33/385
See application file for complete search history.

(56) References Cited

U.S. PATENT DOCUMENTS

| | | | |
|---|---|---|---|
| 2007/0244385 A1* | 10/2007 | Satragno | G01R 33/383 600/410 |
| 2010/0102811 A1* | 4/2010 | Demas | G01R 33/485 324/309 |
| 2015/0177343 A1* | 6/2015 | Wald | G01R 33/28 324/309 |
| 2016/0069968 A1 | 3/2016 | Rothberg et al. | |
| 2018/0143274 A1 | 5/2018 | Poole et al. | |
| 2022/0311383 A1* | 9/2022 | Yu | H03B 5/1243 |

* cited by examiner

POINT-OF-CARE MAGNETIC RESONANCE IMAGING SYSTEM FOR LUMBAR PUNCTURE GUIDANCE

CROSS-REFERENCE TO RELATED APPLICATIONS

This application represents the U.S. national stage entry of International Application No. PCT/US2021/029193 filed Apr. 26, 2021, which is based on and claims the benefit of U.S. Provisional Patent Application Ser. No. 63/015,266, filed on Apr. 24, 2020, and entitled "POINT OF CARE MAGNETIC RESONANCE IMAGER FOR LUMBAR PUNCTURE (LP) GUIDANCE." The contents of these applications are incorporated herein by reference in their entirety.

STATEMENT REGARDING FEDERALLY SPONSORED RESEARCH

This invention was made with government support under EB018976 awarded by the National Institutes of Health. The government has certain rights in the invention.

BACKGROUND

Lumbar punctures ("LP") can be used for both diagnostic uses (e.g., sampling CSF) and therapeutic purposes (e.g., such as alleviating intercranial pressure ("ICP") or delivering drugs or anesthetics). Diagnostically, LP is routine within large hospitals to rule out meningitis and encephalitis, diagnose subarachnoid hemorrhage, examine fevers with central nervous system signs and symptoms, diagnose CNS lymphoma, and provide prognostication in multiple sclerosis. Current therapeutic delivery focuses mainly on pain relief, but also on delivering chemotherapy and antibiotics. However intrathecal administration is poised to have an expanding role in delivering drugs to the CNS with genetic editing therapies (e.g. spinal muscular atrophy) and drugs that have poor blood brain barrier penetration. LP has also emerged as a premiere diagnostic tool for Alzheimer's Disease ("AD"), where protein CSF biomarkers have been useful in predicting future progression in patients with mild cognitive impairment.

Despite its ubiquitous use, the LP is considered difficult to teach because it is purely guided by palpation without visualization of the internal anatomy, leading to repeat attempts and/or avoidance in difficult cases. Image guidance with ultrasound and x-ray is possible, but ultrasound has poor depth resolution and cerebrospinal fluid ("CSF") contrast, and radiation from x-ray complicates point-of-care ("POC") use.

Thus, there remains a need to provide image guidance of LP procedures that is portable, lightweight, and low-cost in order to enable safe and routine POC use.

SUMMARY OF THE DISCLOSURE

The present disclosure addresses the aforementioned drawbacks by providing a magnet assembly for a portable magnetic resonance imaging ("MRI") system. The magnet assembly includes a plurality of magnet blocks configured to create a single-sided permanent magnet. The plurality of magnet blocks are arranged in concentric rings in each of at least two layers to define a central aperture extending through the at least two layers, where the central aperture is sized to receive a medical instrument.

It is another aspect of the present disclosure to provide a portable MRI system that includes a magnet assembly, at least one gradient coil, and a radio frequency ("RF") coil. The magnet assembly extends from an inner, patient-facing surface to an outer surface, and includes a plurality of magnet blocks configured to create a single-sided permanent magnet. The plurality of magnet blocks are arranged in concentric rings in each of at least two layers, where the arrangement of the plurality of magnet blocks is configured to optimize homogeneity over a target field-of-view for spinal imaging. A central aperture extends from the patient-facing surface to the outer surface and is sized to receive a medical instrument. The at least one gradient coil is arranged adjacent the outer surface of the magnet assembly, and the RF coil is arranged adjacent the patient-facing surface of the magnet assembly.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are a single-sided magnet and magnetic resonance imaging ("MRI") system that are portable, lightweight, and low cost and may be used as a point-of care ("POC") MRI device. The portable single-sided MRI system is low-field and may be used to perform three-dimensional ("3D") imaging, two-dimensional ("2D") imaging, or one-dimensional ("1D") imaging.

The portable MRI system may be placed next to a patient during an operation or other medical procedure and, unlike conventional MRI systems, does not require the patient to be transported from a hospital bed to the MRI system and moved into the magnet of the MRI system. The portable MRI system has a lightweight magnet (e.g., less than 25 kg) and dimensions that allow it to easily be moved through doors and into tight spaces.

In an embodiment, the portable MRI system is also low cost, for example, by using magnet materials that only cost on the order of hundreds of dollars. The portable MRI system is configured to provide MRI of tissues such as the spinal cord. In an embodiment, imaging of the tissues is to a depth of 8 cm.

The disclosed portable, point-of-care MRI system may increase the utility of MRI by extending its reach and enabling applications such as providing MRI guidance of lumbar puncture ("LP") procedures, whether for diagnostic or therapeutic purposes.

Advantageously, the portably MRI system reduces barriers to performing this LP and other important diagnostic and drug delivery procedures outside of central hospital settings, expanding its availability to a broader range of healthcare locations and increasingly inexpert staff. While already routinely used to diagnose several conditions, the need for routine LP is poised to dramatically expand in the diagnosis of Alzheimer's Disease, where protein CSF biomarkers accessed through LP have emerged as a premiere diagnostic tool for predicting future progression. LP is also expected to see increasing use for CNS delivery of gene editing therapies and drugs that have poor blood brain barrier penetration.

Although routinely performed, LP is conventionally guided by palpation without visualization of the internal anatomy. This can lead to clinician anxiety and avoidance and repeated puncture attempts in difficult cases. Ultrasound and x-ray have been used to guide LP, but both have significant shortcomings. Ultrasound imaging cannot see the CSF target and the ionizing nature of x-rays is difficult to manage in routine POC use. In contrast, the portable MRI system described in the present disclosure enables both streamlined LP procedures within a hospital and enables it to be performed outside central hospital settings or by inexpert staff.

Figure 1:
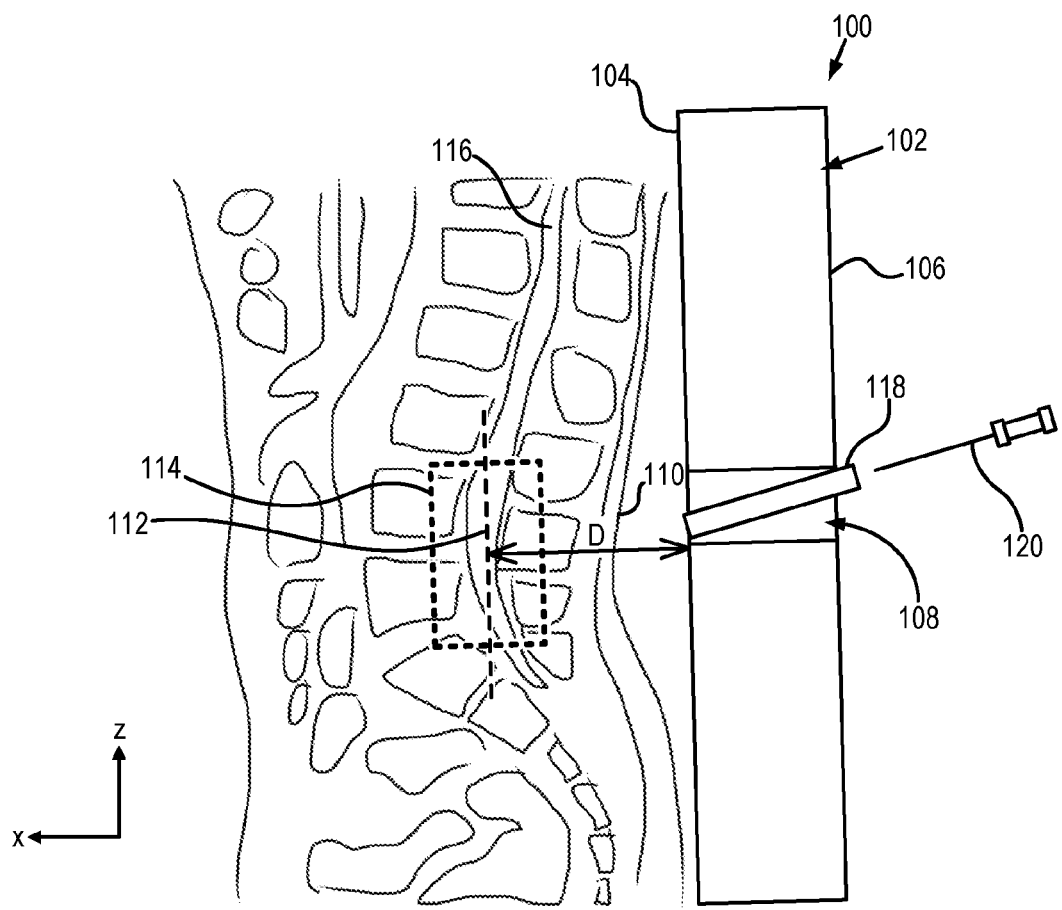
FIG. 1 is a schematic diagram showing a magnet for a portable MRI system used for spinal imaging for guiding the placement of a needle during a lumbar puncture ("LP") procedure.

In some embodiments, the portable MRI system described in the present disclosure integrates a lightweight (e.g., less than 25 kg) device for MRI of the spine and surrounding tissues with a mechanically-constrained 22-gauge needle insertion, thereby guaranteeing registration between the image and needle path without requiring real-time imaging of the needle. During use, the practitioner positions the portable MRI system's central ~2 cm diameter needle insertion hole over the standard needle entry mark between L4 and L5 (FIG. 1). Next, a set of anatomical T2 weighted images can be acquired, on which the expected path of the needle can be plotted. Based on the image plan, a mechanical needle guidance track is set to the planned path avoiding vertebrae and any calcifications in the ligamentum flavum. The maximum depth is planned to just enter the T2-bright subarachnoid space. With the angulation and depth-stop set, the practitioner manually pushes the needle in along this track.

The portable MRI system uses a built-in gradient for readout encoding (or slice-select encoding), and an external gradient coil (e.g., an approximately planar gradient coil) for phase-encoding. As described above, with the needle track mechanically registered to the portable MRI system, the practitioner can pre-visualize the needle path relative to the targeted subarachnoid space, avoiding vertebral bodies and calcifications of the ligaments. Since the target CSF is readily visible on T2 images, the target depth can be determined, and the user can set a mechanical stop on the insertion device to place the needle tip just inside the arachnoid space. This helps minimize disruption of the cauda equina fibers and avoid over-shooting the target and puncturing a vertebral disk. It may also reduce the frequency of post-lumbar puncture headache by reducing the number of attempts at puncture. Knowledge of the target depth provided when using the portable MRI system described in the present disclosure can also avoid the need for multiple removals of the needle's stylet to check for CSF as the needle advances.

Referring now to FIG. 1, in one embodiment, the portable, single-sided MRI system is configured for reduced field-of-view spinal imaging and capable of high resolution one-dimensional (1D), for example, depth profiling, to three-dimensional (3D) imaging. The MRI system includes a lightweight single-sided permanent magnet. FIG. 1 is a schematic diagram showing a magnet for a portable MRI system 100. In FIG. 1, a single-sided magnet 102 (a $B_0$ magnet) has an inner, patient-facing surface 104, an out surface 106, and a central aperture 108 formed therebetween. The patient-facing surface 104 of the magnet 102 can have a generally planar shape to allow the magnet 102 to be positioned adjacent a patient's back 110. When so arranged, the central aperture 108 allows access of a medical instrument, such as a needle, to advance to a target location at or near the patient's spine. For instance, the medical instrument can be advanced to a desired depth 112 (D) measured from the patient-facing surface 104 of the magnet 102 and located within the ROI 114 imaged by the MRI system 100. The magnet 102 can be designed such that the sensitive ROI 114 is sized and positioned to encompass the spinal cord 116 when the magnet 102 is positioned adjacent the patient's back 110.

In an embodiment, the magnet 102 is designed to closely fit adjacent the patient's back 104 in order to maximize the $B_0$ field strength. In some instances, the magnet 102 can be mounted on an articulating arm such that the magnet 102 can be arranged adjacent the patient's back 110 with a hands-free operation. Additionally or alternatively, the magnet 102 can be arranged adjacent the patient's back 110 and then secured in place by strapping the magnet 102 to the patient.

Figure 2:
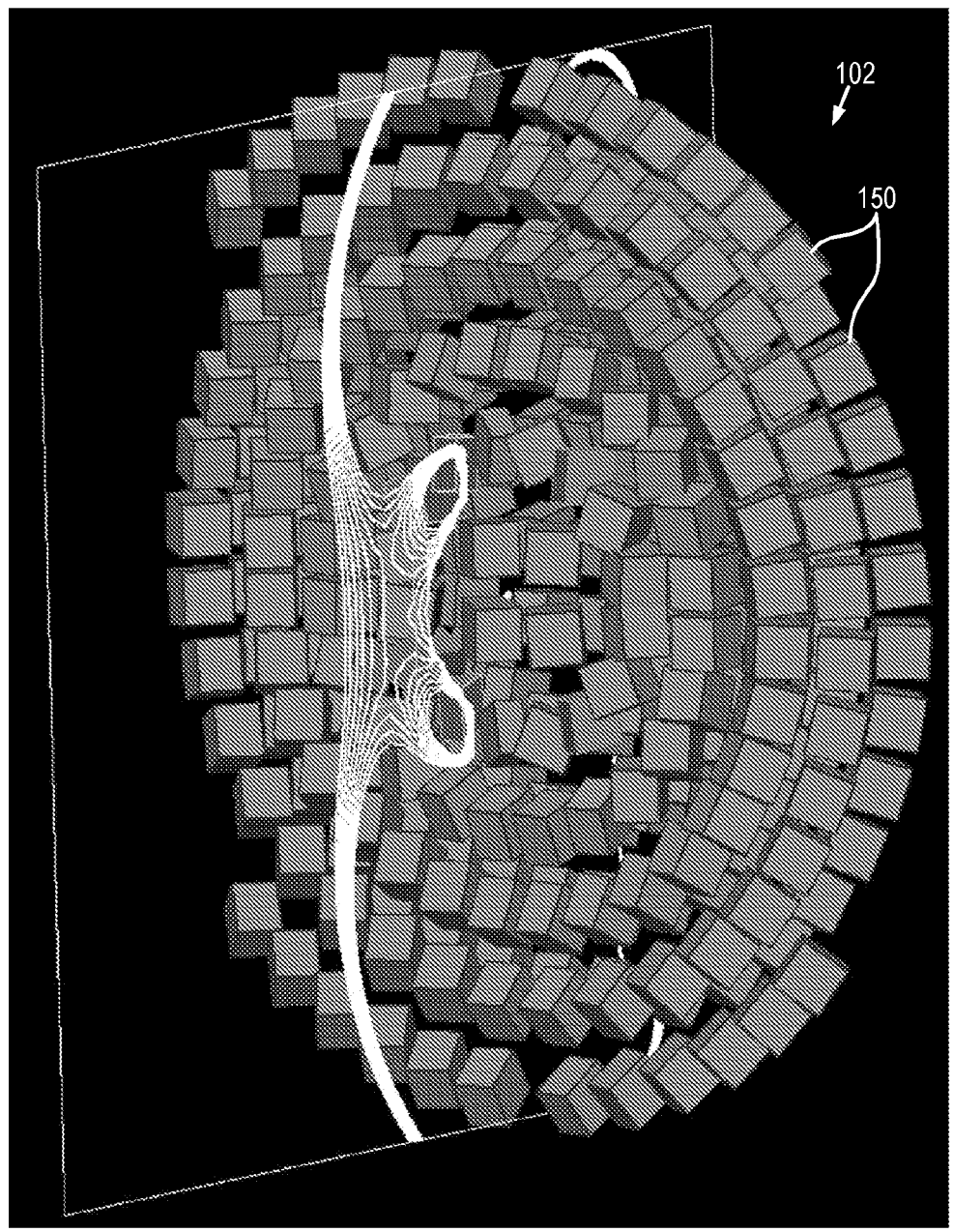
FIG. 2 is a diagram of a portable magnet in accordance with an embodiment. The magnet reaches 40 mT at the target ROI using 248 N52 NdFeB blocks. The magnetic field is shown with isocontours spaced 0.5 mT apart.
Figure 3:
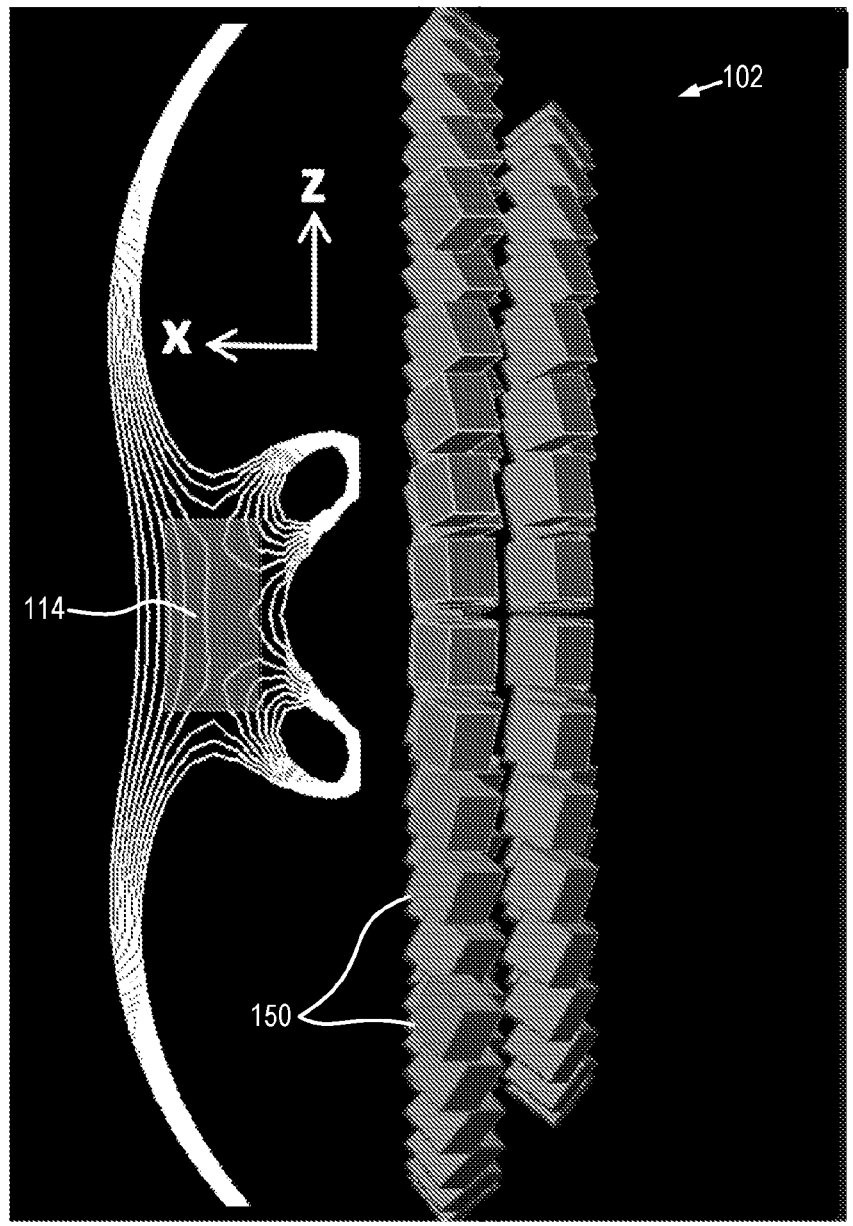
FIG. 3 is a side view of the portable magnet shown in FIG. 2.

As discussed further below, the magnet 102 is designed from a plurality of rare-earth (e.g., NdFeB) permanent magnet blocks arranged in a layered configuration on a former. As a non-limiting example, the magnet 102 can be constructed to have two or more layers of magnet blocks, where the magnet blocks are arranged in concentric rings within each layer, as shown in FIGS. 2 and 3. In such configurations, the concentric rings are coaxial with the central aperture 108. The magnet 102 has a transverse-oriented $B_0$ field with the imaging ROI 114, which can be positioned to include part of the subject's spine and spinal cord 116. Shown in FIG. 1 for reference are an x-axis 118 and a z-axis 120.

In an embodiment, the sensitive volume of the magnet 102 may extend 8 cm into the patient's back 110, such that the imaging ROI 114 contains the patient's spinal cord 116 to facilitate guidance of a medical instrument, such as a needle. An MRI system utilizing magnet 102 may be used for spinal imaging over a 3D volume and may include gradient coils (not shown) placed external to the magnet 102 on the outer surface 106 and an RF coil (not shown), which in some embodiments may be positioned on the inner, patient-facing surface 104 of the magnet 102. In an embodiment, the shape of the ROI 114 may be configured to match the $B_1$ sensitivity profile of the RF coil used for imaging.

As described above, a guidance track 118 can be coupled to the magnet 102, for instance by coupling the guidance track 118 to the central aperture 108 of the magnet 102. The guidance track 118 provides a mechanical guide to advance a medical instrument, such as a needle 120, along a trajectory whose position and orientation is known relative to the magnet 102 by way of coupling the guidance track 118 to the magnet 102. By knowing the spatial relationship between the magnet 102 and the guidance track 118, the portable MRI system 100 is capable of imaging the ROI 114 and visualizing or otherwise overlaying the trajectory defined by the guidance track 118 on the images of the ROI 114. In this way, the precise placement of the needle 120 can be visualized prior to inserting the needle 120 into the guidance track 118 and advancing the needle 120 into the patient.

FIGS. 2 and 3 are diagrams showing a portable magnet 102 in accordance with an embodiment. In an embodiment, the portable magnet 102 may have dimensions so that it may be held by hand. As mentioned, the inner, patient-facing surface 104 is designed to be generally planar with the patient's back. As mentioned, the portable MRI magnet 102 may be used in an MRI system configured for reduced field-of view spinal imaging.

Figure 4:
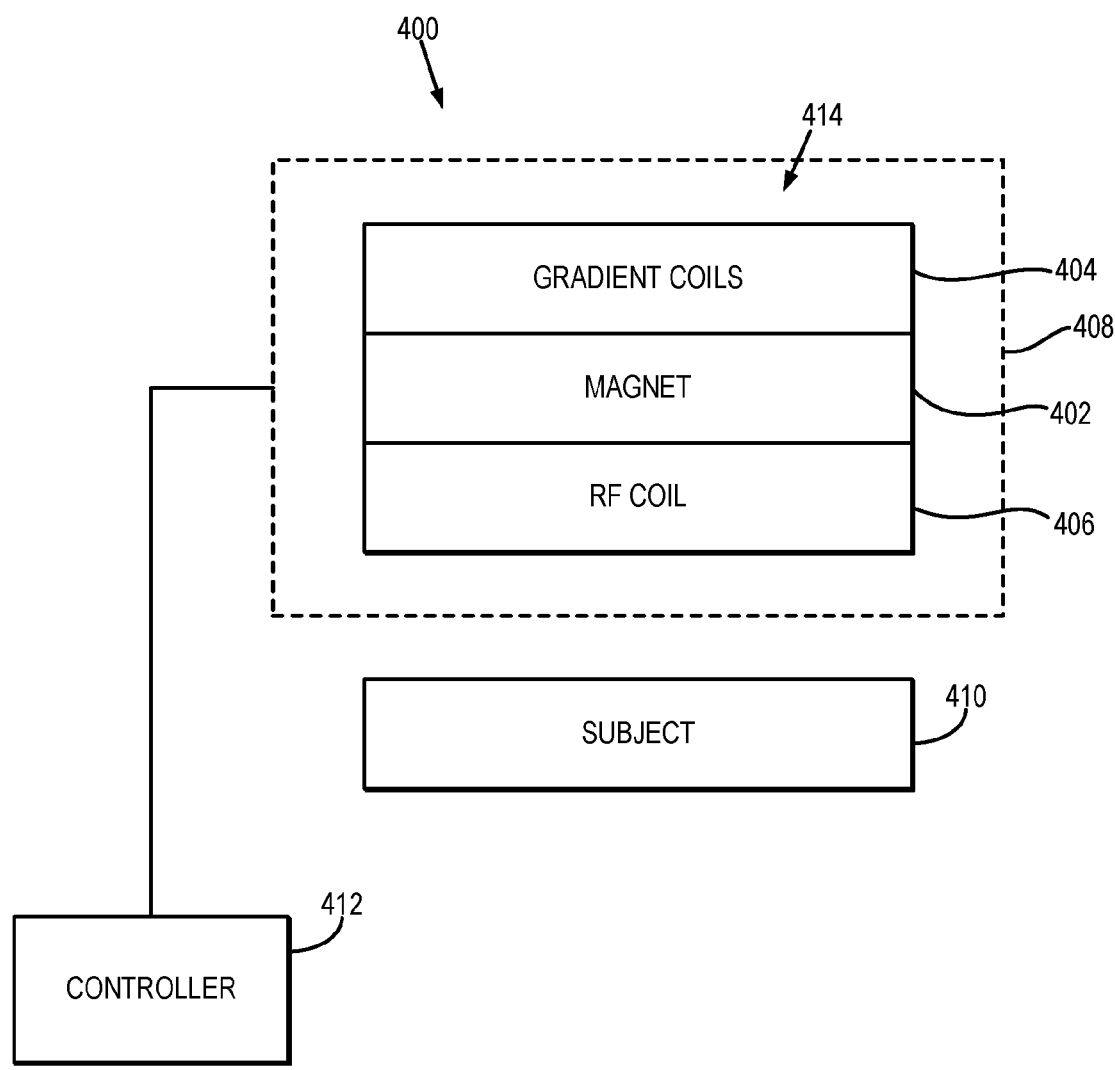
FIG. 4 is a schematic block diagram of a portable MRI system in accordance with an embodiment.

FIG. 4 is a schematic block diagram of a portable MRI system 400 in accordance with some embodiments described in the present disclosure. In FIG. 4, a schematic representation of the position of various elements in the MRI system 400 with respect to one another is shown using blocks rather than the specific shape described above. The MRI system 400 includes a magnet assembly 414 having a magnet 402, gradient coils 404, and an RF coil 406 disposed within a housing 408 and positioned in close proximity to or on (e.g., close fitting) a subject 410. The magnet 402 is a single-sided magnet. As one non-limiting example, the single-sided magnet 402 is designed from a plurality of permanent magnet blocks (e.g., NdFeB permanent magnet blocks) arranged in a layered configuration on a former. The layered configuration can include two or more layers of permanent magnet blocks. As one example, the layered configuration can include two or more layers of permanent magnet blocks arranged in concentric rings within each layer. In one specific embodiment, such as the example shown in FIGS. 2 and 3, the layered configuration can include two layers of concentric rings.

Single-sided magnets typically have large field gradients moving away from the magnet surface. This built-in $B_0$ gradient may be used for readout and slice select encoding. The magnet 402 may also be designed to avoid very strong (e.g., greater than 1 T/m) gradients. Gradient coils 404 can also be configured to be positioned on the outer surface (e.g., surface 106 shown in FIG. 1) of the magnet 402. For example, a pair of gradient coils may be used to enable phase encoding on the other two directions that are orthogonal to the readout direction. The RF coil 406 is configured to be positioned on an inner surface (e.g., surface 104 shown in FIG. 1) of the magnet 402. The RF coil 406 may be used to provide excitation and RF signal detection. In other embodiments, separate RF coils can be provided for excitation and signal detection. As discussed further below, the assembly of the magnet 402, gradient coils 404, and RF coil 406 can each include a former (not shown) on which the permanent magnet blocks, gradient coils, and RF coil(s) are mounted.

A controller 412 is coupled to the magnet 402, gradient coils 404, and RF coil 406 and configured to control the operation of the magnet 402, gradient coils 404, and RF coil 406 to acquire MR images of the subject 410. For example, controller 412 is configured to drive the gradient coils 404 and RF coil 406 for gradient waveform generation and RF waveform generation, respectively, using known hardware and methods. In addition, controller 412 is configured to record MR signals received by the RF coil 406 from the subject 410. Controller 412 may also be configured to generate images based on the received MR signals using known reconstruction methods.

Figure 5:
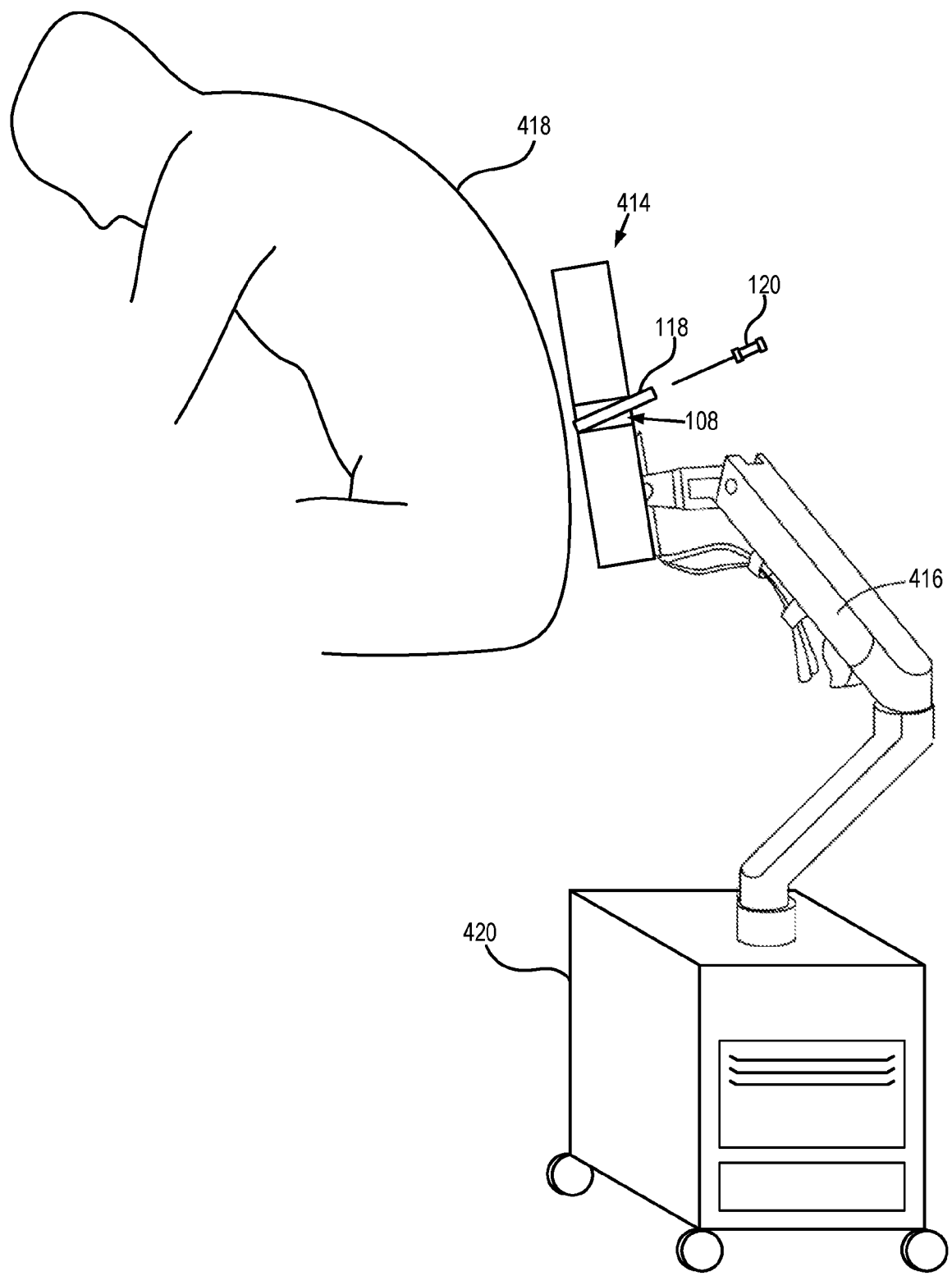
FIG. 5 is a schematic diagram of a portable MRI system and an articulated arm in accordance with an embodiment.

In an embodiment, such as the one shown in FIG. 5, the magnet assembly 414 containing the magnet 402, gradient coils 404, and RF coil 406 may be attached or otherwise coupled to an articulated arm 416, that allows the magnet assembly 414 to be positioned and moved into place adjacent a patient's back 418. Using the articulated arm, the magnet assembly 414 may be arbitrarily positioned allowing movement of the sensitive volume of the single-sided magnet 402 to the appropriate region to allow for image-guided placement of a medical instrument (e.g., a needle 120) for an LP procedure or other medical procedure. This embodiment may allow the magnet assembly 414 to be, for example, positioned on a moveable cart 420 that can be moved into a patient's room or bedside to facilitate imaging and performance of the LP procedure or other medical procedure without having to move the patient to a dedicated imaging room. In such an example, the controller 412 may be housed within the moveable cart 420. Advantageously, the articulated arm 416 also allows the magnet assembly 414 to be moved into position whether the patient is in a sitting or supine position.

In use, the portable MRI system 400 allows for both imaging and mechanically constraining the needle insertion. Building these together ensures registration between the image and needle path without requiring real-time imaging of the needle. After marking the entry point (e.g., based on standard L4/L5 landmarks), the practitioner wheels the 20-30 kg MRI assembly 414 (on its stand) up to the patient, who can be in the standard left-lateral position placing the approximately 2 cm diameter central aperture 108 for the needle 120 over the mark. The magnet assembly 414 is supported by the stand (e.g., articulated arm 416) but can be additionally secured to the patient's back 418 with surgical tape. A 3-5 minute set of RARE T2 images of the L4/L5 area is acquired and the expected path of the needle is plotted on these images. Based on the image plan the mechanical needle guidance track 118 is translated and rotated into the proper position to achieve the planned path, including a depth stop to prevent overshooting the subarachnoid space. With the angulation and stop set, the practitioner manually pushes the needle 120 in along this mechanically set track. Since the insertion is manual (but mechanically confined to the chosen path) the practitioner feels the needle 120 passing the expected landmarks similar to an unguided procedure.

As mentioned above, the portable, single-sided magnet 102 (shown in FIG. 1) is designed from a plurality of permanent magnet blocks arranged in a layered configuration on a former and may be used to obtain images of a spinal region of a subject that it is positioned adjacent. In an embodiment, the arrangement of the plurality of rare-earth permanent magnet blocks is optimized for the layered configuration. For example, the magnet may be designed with a genetic algorithm optimizing homogeneity over a field-of-view ("FOV") and the built-in gradient for slice-selection or readout encoding. For example, the placement of the rare-earth magnet material (e.g., NdFeB) may be chosen using the genetic optimization framework.

In an embodiment, a magnet array containing N=248 N52-NdFeB magnets arranged in two layers in concentric rings and arcs was optimized, as shown in FIGS. 2 and 3.

Individual magnet blocks were all 25.4×[y]×25.4 mm³, where the [y]-dimensions were numerically optimized in a continuous range of 0-25.4 mm. The magnet was designed with symmetry about the XY and XZ planes to produce an x-oriented $B_0$ field gradient (i.e., directed into the patient's back).

The sizes and angular orientations of the magnet blocks were optimized to produce a 4×6×8 cm³ homogeneous magnetic field along the spine at a depth of 8 cm from the magnet surface (e.g., the patient-facing surface 104 in FIG. 1) and overlaying the adult L3-L5 spine (as shown in FIG. 1). As an example, the optimization can be performed by finding the minimum of a constrained nonlinear multivariable function. As a non-limiting example, the "fmincon" tool in MATLAB (Mathworks) can be used with: cost function–range of $B_0$ magnitude (fcost=range{|B–0|}), computed at points on a 1 cm³ grid within the ROI; constraints–mean |B0|>=40 mT, 0<=y<=25.4 mm. Magnet blocks can be modeled as L=5 multipole field sources for field computation during optimization. Simulated $B_0$ maps for the optimized design can be computed using Biot-Savart simulation software (e.g., Ripplon).

Figure 6:
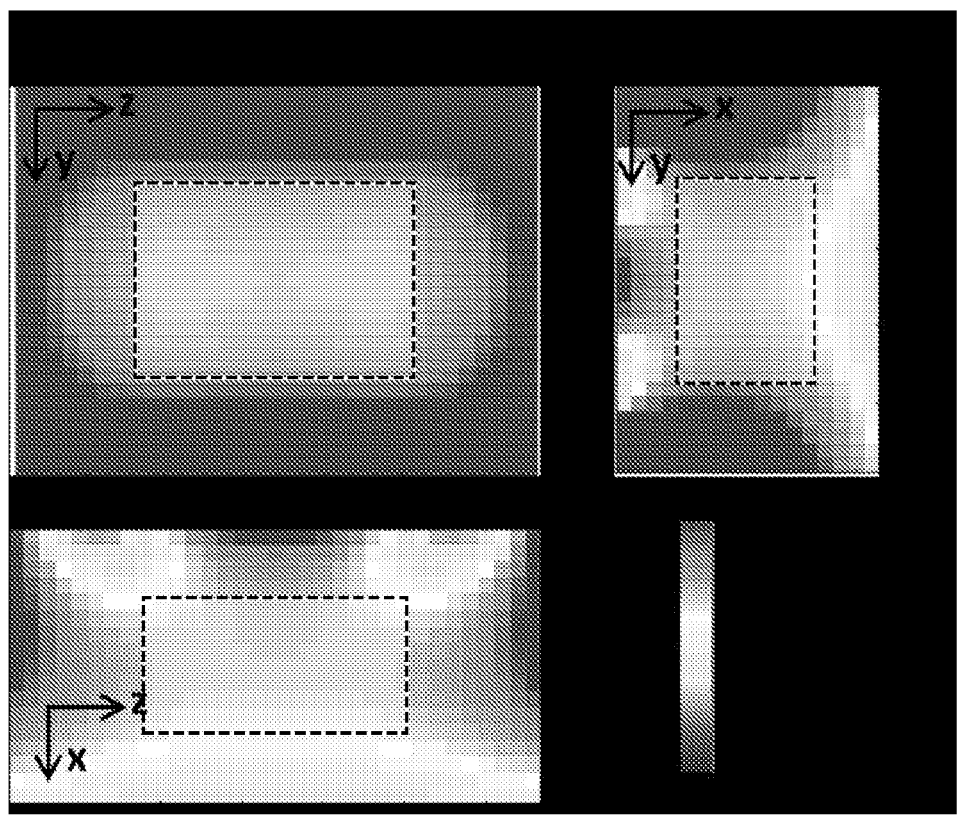
FIG. 6 shows simulated field maps in three planes for the LP-guided magnet design. The dashed box represents the target ROI. In the ROI the mean field is ~40 mT and the gradient is approximately 50 mT/m.
Figure 7:
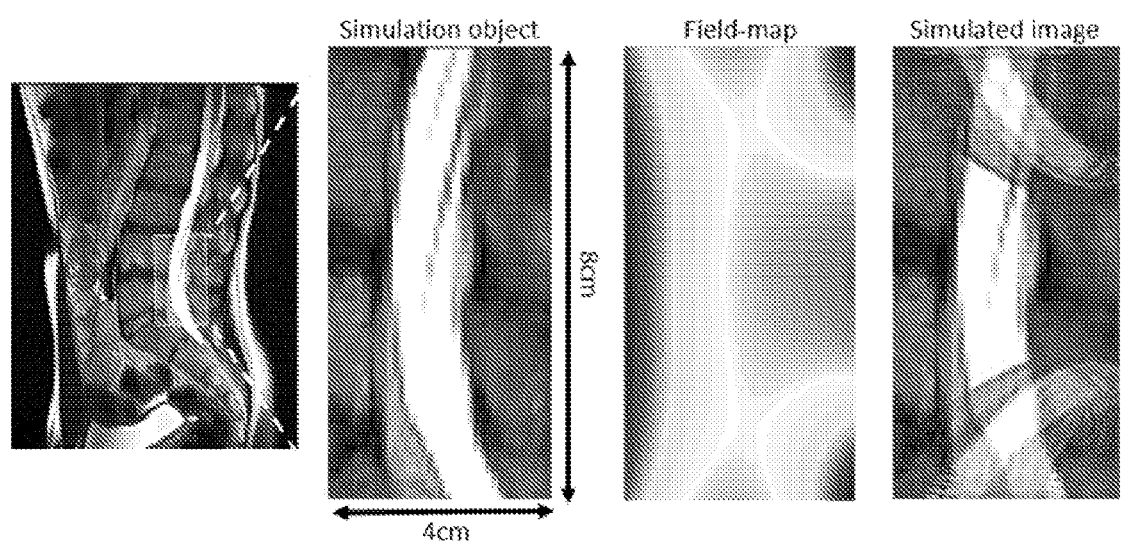
FIG. 7 shows simulated images based on the field maps of FIG. 6 for the LP guided magnet initial design. The field pattern, supports some aliasing in the image, but the L4/L5 region is clear. Aliasing can be potentially addressed in magnet design and by using an Rx receive array.

The magnet can be designed to acquire a ~3 minute duration 3D RARE spin-echo image with the $G_x$~50 mT/m built-in read-out gradient, $G_y$ phase encoding along the echo-train, and $G_z$ phase encoding shot-to-shot. A 2D imaging simulation was performed using the XZ field-map shown in FIG. 6 for $G_x$ and a linear planar gradient coil producing $G_z$=8 mT/m peak for the Z phase encode. The simulation FOV is 4 cm×8 cm, with 256 readout points, BW=50 KHz, and 97 phase-encodes in Z. FIG. 7 shows simulated images based on the above field maps for the LP guided magnet initial design. The simulation object is a T2-weighted MR image of the target ROI (around the subarachnoid space between L4 and L5). The simulated image exhibits aliasing due to the non-bijective pattern in the $B_0$ field-map. However, the L4/L5 region is clear and enables mechanical guidance via the needle track. The aliasing could potentially be addressed using multiple surface coils and/or by optimizing the magnet with a cost function that includes encoding performance.

In an embodiment, the continuous magnet material section of a Halbach magnet approximates the desired magnet shape (i.e., layers of concentric rings) and $B_0$ direction. The continuous magnetization pattern can then be discretized into a plurality of blocks. The discretized Halbach section approximates the continuous magnetization pattern as an assembly of magnet blocks. The discretized Halbach section is practical to construct and has the desired field orientation but is not optimized for in-plane homogeneity or gradient strength. In an embodiment, the optimization may be performed by allowing the genetic algorithm, or other optimization algorithm, to alter the sizes, block magnetization grade, compositions, and translational position of each magnet block.

The optimal magnet design may then be converted into a physically-realizable assembly of permanent magnet blocks, as shown in FIGS. 2 and 3. The example optimized magnet 102 shown in FIGS. 2 and 3 is shown as an assembly of standard size and standard material NdFeB blocks 150. The magnet assembly can include magnet blocks of various size and material combinations including N52 blocks of size 1×1×1⅛ in³, N52 blocks of size 1×1×1⅜ in³, N42 blocks of size 1×1×1 in³, N45 blocks of size 1×1×⅜ in³, or other such sized blocks as may be determined through the optimized magnet design. In an embodiment, some blocks may be constructed by sticking multiple smaller blocks together (e.g., an N52 1"×1"×1⅛" block contained an N52 1"×1"×1" block and an N52 1"×1"×⅛" bock).

In the example shown in FIGS. 2 and 3, the magnet assembly is shown with 0.5 mT magnetic field iso-contours. The magnet measures 8×42×50 cm³, contains 24.2 kg of rare-earth material, and produces a mean field of 40.9 mT in the target ROI. FIG. 6 shows the simulated magnetic field-maps in the three Cartesian planes with the dashed boxes indicating the target ROI.

A former is used to hold the magnet blocks prescribed by the optimized design. For example, the former can be constructed to include slots that are sized, positioned, and shaped to receive the magnetic blocks in an optimized magnet design. The magnet former may be constructed of a material such as acrylic. In an embodiment, the magnet former is constructed using 3D printing. The magnet former includes a plurality of slots. The final assembled magnet bocks are inserted into the slots of the magnet former and may be secured to the former using, for example an epoxy.

As mentioned, the portable magnet assembly may include a pair of gradient coils (e.g., gradient coils 404 shown in FIG. 4). In an embodiment, one or more planar-shaped gradient coils are provided that are configured for phase encoding (e.g., phase encoding along the y- and z-axes). The gradient coils are constructed on a gradient coil former that may be positioned on an outer surface of the magnet. This design saves valuable space within the magnet to enable a stronger $B_0$ and allows for improved gradient linearity, at the cost of reduced gradient efficiency. In addition, weak unshielded gradient coils do not produce significant eddy current effects if placed either inside or outside an NdFeB magnet.

In an embodiment, the gradient winding patterns for the $G_y$ and $G_z$ gradient coils can be designed using a modified Boundary Element Method ("BEM") stream function with L1-regularization. The target fields for the $G_y$ and $G_z$ coils can include both the desired linear terms (Y and Z, respectively) and an additional 2nd-order term (XY and XZ, respectively). The efficiency of a single-sided gradient coil decreases as one moves away from it (in this case, along the x-direction), and this decrease is manifested as undesired XY and XZ terms for the $G_y$ and $G_z$ coils, respectively. The addition of the 2nd-order terms in the target field of the BEM stream function design helps compensate for the spurious XY and XZ terms improving linearity over the target ROI.

The optimized stream functions can then be converted into wire winding paths. To construct the gradient coils, the optimized stream functions (winding paths) can be projected onto a piecewise-linear surface of a gradient coil former. In an embodiment, a gradient coil former may be constructed by 3D printing a polycarbonate disc, slab, or other appropriately shaped former (e.g., ~2 mm thick). The former contains wire grooves that correspond to the numerical winding paths computed from the stream function. The wire grooves are configured to receive magnet wire, for example, the wire grooves may be configured for press-fitting two layers of magnet wire into the polycarbonate former. The completed $G_y$ and/or $G_z$ gradient coils and former assembly can then be positioned around a magnet, such as at the outer surface 106 of the magnet 102 shown in FIG. 1.

As mentioned, the portable magnet assembly may also include an RF coil (e.g., RF coil 136 shown in FIG. 4). An RF coil assembly may be constructed by designing an RF coil (or winding) on a surface (or RF coil former) configured to fit inside the $B_0$ magnet. In an embodiment, the RF coil may be designed using the same BEM stream function approach described above with respect to the gradient coils.

The same static-field approach used for the gradient design may be used because the RF coil dimension (~0.1 m) may be much less than the wavelength at the Larmor frequency. An RF coil winding may be designed to optimize spatial B1 uniformity within the target ROI (e.g., ROI 114 shown in FIG. 1). The RF coil may be constructed by press-fitting wire (e.g., Litz wire).

The MRI system described herein may be used as a point-of-care system to acquire 1D and 3D images, for example of the spine and spinal cord, over a reduced FOV sensitive region in order to facilitate the guidance of a medical instrument (e.g., a needle) during a procedure (e.g., an LP procedure). In an embodiment, a shimming capability may be applied to the $B_0$ magnet or the optimization may more explicitly penalize peak ("min-max") inhomogeneities to mitigate any reduction of the slice thickness or signal level. In another embodiment, gradient non-linearity effects may be mitigated by refining the gradient coil design or compensated for in the pulse sequence by adjusting the encoded FOV for each slice. Other options include post-processing approaches which apply a gradient nonlinearity correction or generalized image reconstruction approach.

In an embodiment, control of the built-in $B_0$ gradient is used to provide equal amounts of signal per bandwidth at different positions in the ROI. An improved magnet design with higher linearity (but limited gradient strength) may be used to mitigate artifacts. Additionally, an RF coil with increased spatial uniformity and coverage may improve images. In an embodiment, this may be achieved by either a physically larger RF coil or an RF coil with more windings. Adding winding of increasing size boosts the inductance of the coil more quickly than the resistance. However, this in turn would increase the Q of the coil and decrease its bandwidth, exacerbating any coil BW issue. Resolving issues stemming from narrow coil bandwidth may be approached by shaping the spectral resonance response of the coil. On approach for creating an RF coil with a more uniform frequency response is using a series resistor. Several approaches for creating a coil with a more uniform frequency response without a series resistor include quasi-transmission line coils, coupled resonant structures, used of a low-impedance preamplifier, and inductively coupled negative feedback mechanisms.

In an embodiment, image signal-to-noise ratio ("SNR") may be improved either with improved system hardware or an improved acquisition. For example, either a stronger $B_0$ magnet or more uniform $B_0$ magnet (enabling reduced-bandwidth acquisitions) would improve SNR. A stronger $B_0$ magnet in the same form factor may be achievable by allowing for a higher density of magnetic material or by adding an additional layer of magnet blocks or otherwise increasing the thickness of the magnet. A more uniform magnet may be realized by the use of $B_0$ shim coils or shim material. An improved RF coil may also be used to increase SNR.

In an embodiment, weighting the sampling density to the center of k-space or utilizing sparsity priors such as compressed-sensing type acquisitions or denoising approaches may be used to boost SNR. In another embodiment, for an acquisition using a RARE pulse sequence a flipback pulse after each RARE train may assist with longitudinal magnetization recovery and increase available signal.

In an embodiment, the portable MRI system may also include shielding, for example, either a passive shielding approach such as draped conductive cloth, or an active interference cancellation system. In another embodiment, to address temperature induced drift in $B_0$, various approaches may be used including a feedback system controlling a heater to stabilize the temperature, use of a combination of rare-earth materials with differing temperature coefficients, or the use of a field probe to measure $B_0$ drift for incorporation into a model-based image reconstruction algorithm.

As mentioned, the portable $B_0$ magnet MRI system may be used for reduced-FOV imaging of the spine and spinal cord to guide the placement of a medical instrument, such as a needle, during a procedure.

The $B_0$ magnet may be designed by optimizing the distribution of rare-earth magnets needed to maximize homogeneity over a target ROI. In an embodiment, an interior point method may be used to optimize magnet block size (and thus magnetic dipole size) for a layered Halbach geometry. The three components of a magnetic dipole moment vector are optimized at points on a planar or other suitably shaped surface that can be arranged adjacent a patient's back to design a magnet assembly that minimizes the absolute range of $B_0$ magnitude over a target ROI. In a non-limiting example, the optimization can implement a minimum mean $B_0$, and constrain all magnetic dipole moment vector magnitudes be less than that of a 1"×1"×1" block of N53 magnet material. The optimization used an initial guess solution. For example, the optimization may use a "test-tube magnet" as an initial guess solution. In this optimization, each magnet block in the assembly can be modeled as an ideal point dipole source. Next, each dipole moment vector in the optimized solution can be uniformly scaled up until the dipole moment with the largest magnitude matched that of a 1"×1"×1" block of N52-grade NdFeB material. A design was then generated containing the prescribed number of non-intersecting N52 magnet blocks of differing volume, such that each block's magnetic dipole moment matched that generated by the numerical optimization.

Computer-executable instructions for optimizing the design of a portable magnet and MRI system and for operating a portable MRI system according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present disclosure has described one or more preferred embodiments, and it should be appreciated that many equivalents, alternatives, variations, and modifications, aside from those expressly stated, are possible and within the scope of the invention.

The invention claimed is:

1. A magnet assembly for a portable magnetic resonance imaging (MRI) system, the magnet assembly comprising:
   a plurality of magnet blocks configured to create a single-sided permanent magnet, the plurality of magnet blocks being arranged in concentric rings in each of at least two layers to define a central aperture extending through the at least two layers, wherein the central aperture is sized to receive a medical instrument.

2. The magnet assembly of claim 1, wherein the central aperture is sized to receive a medical instrument comprising a needle.

3. The magnet assembly of claim 1, wherein the central aperture is sized to receive a medical instrument comprising a needle guidance track.

4. The magnet assembly of claim 1, wherein the central aperture has a 2 cm diameter.

5. The magnet assembly of claim 1, wherein the plurality of magnet blocks is arranged in concentric rings in each of two layers.

6. The magnet assembly of claim 5, wherein the two layers comprise a first layer that is parallel with a second layer.

7. The magnet assembly of claim 6, wherein the first layer and the second layer are planar layers.

8. The magnet assembly of claim 1, wherein angular orientations of the plurality of magnet blocks are varied in each concentric ring.

9. The magnet assembly of claim 1, further comprising a former having a plurality of slots, wherein each of the plurality of magnet block is positioned in one of the plurality of slots.

10. The magnet assembly of claim 1, wherein the plurality of magnet blocks is arranged in a configuration that optimizes magnetic field homogeneity over a target field-of-view for spinal imaging.

11. The magnet assembly of claim 10, wherein the plurality of magnet blocks is configured such that the target field-of-view is positioned at a distance of 80 mm from a surface of the magnet assembly.

12. The magnet assembly of claim 1, wherein a weight of the magnet assembly is between 20 kg and 30 kg.

13. The magnet assembly of claim 1, wherein the plurality of magnet blocks is further arranged to generate a magnetic field gradient along a direction for slice selection or readout encoding.

14. A portable magnetic resonance imaging (MRI) system comprising:

a magnet assembly extending from an inner surface configured to face a patient to an outer surface, the magnet assembly comprising:
 a plurality of magnet blocks configured to create a single-sided permanent magnet, the plurality of magnet blocks being arranged in concentric rings in each of at least two layers, wherein the arrangement of the plurality of magnet blocks is configured to optimize homogeneity over a target field-of-view for spinal imaging;
 a central aperture extending from the patient-facing surface to the outer surface and sized to receive a medical instrument;
at least one gradient coil arranged adjacent the outer surface of the magnet assembly; and
a radio frequency (RF) coil arranged adjacent the patient-facing surface of the magnet assembly.

15. The portable MRI system of claim 14, further comprising a controller coupled to the magnet assembly, the at least one gradient coil, and the RF coil.

16. The portable MRI system of claim 14, further comprising:
a housing disposed around the magnet assembly, the at least one gradient coil, and the RF coil; and
an articulated arm coupled to the housing.

17. The portable MRI system according to claim 14, wherein the target field of view is 3 cm×8 cm×8 cm.

18. The portable MRI system according to claim 14, wherein the arrangement of the plurality of magnet blocks is further configured to generate a gradient for slice selection or readout encoding.

19. The portable MRI system according to claim 14, wherein the arrangement of the plurality of magnet blocks generates a sensitive volume that is configured to extend 3 cm beneath a surface of the subject.

20. The portable MRI system according to claim 14, wherein the portable MRI system is configured to acquire three dimensional images.

21. The portable MRI system according to claim 14, wherein the inner surface of the magnet assembly is curved and the outer surface of the magnet assembly is curved.

* * * * *